United States Patent [19]
Pedigrew

[11] Patent Number: 4,675,209
[45] Date of Patent: Jun. 23, 1987

[54] PROCESS AND DEVICE FOR THE APPLICATION OF A HIGH-ACTIVE ABSORBER ON A SUBSTRATE

[75] Inventor: Colin Pedigrew, Erkrath, Fed. Rep. of Germany

[73] Assignee: Nordson Corporation, Amherst, Ohio

[21] Appl. No.: 758,347

[22] Filed: Jul. 24, 1985

Related U.S. Application Data

[63] Continuation of Ser. No. 647,866, Sep. 5, 1984, abandoned, which is a continuation of Ser. No. 424,443, Sep. 27, 1982, abandoned.

[30] Foreign Application Priority Data

Feb. 2, 1982 [EP] European Pat. Off. ........ 82100921.4

[51] Int. Cl.⁴ .......................... B05B 7/00; B05C 5/00; B05D 5/00
[52] U.S. Cl. .................................... 427/194; 118/304; 118/308; 118/312; 118/410; 427/197; 427/198; 427/202; 427/264; 427/368
[58] Field of Search ................... 118/63, 50, 304, 308, 118/312, 410, 411, 653; 427/180, 194, 197, 200, 202, 206, 198, 264, 368

[56] References Cited

U.S. PATENT DOCUMENTS

| | | | |
|---|---|---|---|
| 2,292,596 | 8/1942 | Baechtold | 91/17 |
| 2,789,075 | 4/1957 | Stahl | 154/83 |
| 3,399,671 | 9/1968 | Satas | 128/156 |
| 3,439,650 | 4/1969 | Stowell | 118/637 |
| 3,890,926 | 6/1975 | Teed | 118/325 |
| 4,045,833 | 9/1977 | Mesek et al. | 5/335 |
| 4,156,664 | 5/1979 | Skinner et al. | 260/17.46 C |
| 4,256,526 | 3/1981 | McDaniel | 156/295 |
| 4,352,837 | 10/1982 | Kopenhaver | 427/187 |

FOREIGN PATENT DOCUMENTS

| | | |
|---|---|---|
| 0033235 | 8/1981 | European Pat. Off. |
| 1012428 | 7/1957 | Fed. Rep. of Germany |
| 2222780 | 11/1973 | Fed. Rep. of Germany |
| 3040768 | 9/1981 | Fed. Rep. of Germany |
| 2173059 | 10/1973 | France |
| 1375331 | 11/1974 | United Kingdom |
| 2004201 | 3/1979 | United Kingdom |
| 2061974 | 5/1981 | United Kingdom |

*Primary Examiner*—Michael R. Lusignan
*Attorney, Agent, or Firm*—Wood, Herron & Evans

[57] ABSTRACT

A method for the application of highly absorbent material onto a moving substrate includes the steps of dispensing a melt adhesive film onto precisely defined areas of the substrate, covering such areas with the absorbent material and then removing excess absorbent material which did not adhere to the adhesive coated areas. The apparatus for practicing this method includes, in one embodiment, an adhesive applicator head operable to dispense the adhesive at timed intervals onto the moving substrate, a measuring head located downstream from the applicator head and timed to release the absorbent material over the adhesive covered areas moving past and a vacuum or mechanical cleaning device for removing excess absorbent material from the substrate. In an alternative embodiment, the measuring head is replaced with a receptacle containing absorbent material within which the substrate is immersed for coating the adhesive covered areas. The method and apparatus are particularly adapted for use with conventional machines in the manufacture of hygenic articles such as sanitary pads, tampons, diapers and the like.

5 Claims, 8 Drawing Figures

PROCESS AND DEVICE FOR THE APPLICATION OF A HIGH-ACTIVE ABSORBER ON A SUBSTRATE

CROSS REFERENCE TO RELATED APPLICATION

This application is a continuation of U.S. patent application Ser. No. 647,866, filed Sept. 5, 1984, entitled "Method and Apparatus For Applying An Absorbent Material Onto a Substrate", now abandoned, which was a continuation of Ser. No. 424,443, filed Sept. 27, 1982, now abandoned entitled "Process and Device For The Application Of A High-Active Absorber On A Substrate", now abandoned.

BACKGROUND OF THE INVENTION

This invention is directed to a method and apparatus for the application of a high-active absorber on a substrate, and, more particularly, for increasing the absorbent capacity of substrates forming one or more layers of hygenic articles without increasing their volume.

Hygenic articles such as diapers, sanitary napkins, incontinence pads and sickbed sheets must have a high absorption capacity to effectively retain eliminated body fluids for acceptable periods of time. Early hygenic articles of this type employed cellulose wadding, fluff cellulose or absorbent cotton as absorbent materials. The problem with these materials is that their absorbent capacity is relatively small compared to their volume. In order to improve the absorbent capacity of hygenic articles made from these materials, and retain eliminated body fluids for longer time periods, the volume of absorbent materials in such hygenic article must be increased. Increasing the volume of cellulose or absorbent cotton in hygenic articles such as sanitary napkins and tampons is unacceptable.

Cellulose wadding, fluff cellulose and absorbent cotton have generally been replaced in the manufacture of hygenic articles with highly active absorbent particles, which increase the absorbent capacity of the articles and/or decrease their volume. Such absorbent particles are known in the art and generally consist of water insoluble, water-resisting organic polymers having the shape of fine grain solid material.

One attempt to incorporate high-active absorbent particles in hygenic articles involved imbedding the absorbent particles in a material such as abosrbent cotton. It was found, however, that the absorbent particles tended to cluster in one or more areas of the absorbent cotton instead of throughout the article. This resulted in a hygenic article having good absorbent capacity in some areas, but poor capacity in other areas through which eliminated body fluids were allowed to pass.

One solution to this problem was proposed in German Patent No. DE 30 40 768 in which the absorbent material is imbedded in a coating which is directly applied to the entire area of a hygenic article, such as a diaper or tampon. Alternatively, the absorbent material is used to coat a backing sheet which is then applied to the entire article. Although high absorption capacity in a relatively small volume is achieved with this process, the manufacturing costs are great.

SUMMARY OF THE INVENTION

It is therefore among the objects of this invention to provide a method and apparatus for the application of highly absorbent material to a substrate, particularly a substrate forming one or more layers of hygenic articles, which is economical and which produces hygenic articles having a relatively high absorbent capacity and reduced volume.

These objectives are accomplished in one embodiment of a method according to this invention which comprises the steps of applying a thin film of melt adhesive onto at least one predetermined area of a moving substrate, releasing absorbent particles from a location above the substrate onto the areas covered with adhesive and then removing any excess particles from the substrate which did not adhere to the melt adhesive.

In an alternative embodiment, the method of this invention comprises the steps of applying a thin film of melt adhesive to at least one predetermined area of a moving substrate, directing the substrate into a container at least partially filled with absorbent material, immersing the substrate within the absorbent material in the container so that absorbent material adheres to the predetermined areas covered with adhesive and then removing excess absorbent material from the substrate which did not adhere to the predetermined areas.

The apparatus for accomplishing the firstmentioned method according to this invention comprises an applicator head for applying a thin film of melt adhesive on at least one predetermined area of the substrate moving beneath the applicator head, a measuring head located downstream of the applicator head which is operable to release absorbent particles onto the predetermined areas of the substrate coated with adhesive, and a suction head located downstream from the measuring head for removing excess absorbent particles which did not adhere to the predetermined areas of the substrate.

The latter-mentioned method is practiced with an apparatus according to this invention having an adhesive-applying applicator head which is operable in essentially the same manner as the applicator head described above to form predetermined areas on the substrate coated with a thin film of melt adhesive. In addition, the apparatus of this embodiment includes a container having a pool of absorbent particles through which the substrate is guided and immersed within the absorbent particle pool. The absorbent particles adhere to the predetermined areas of the substrate covered with adhesive, and any excess particles not adhered to such predetermined areas are removed and returned to the container.

One advantage of the method and apparatus of this invention is that the amount and location of the absorbent particles applied to the substrate can be carefully controlled to obtain the required absorption capacity at the desired areas of a hygenic article made from the substrate. Accurate and limited application of melt adhesive films to selected areas of the substrate enables the absorbent particles to be applied to areas of the hygenic article which are exposed to eliminated body fluids. In contrast, prior art methods of applying absorbent particles involved coating the entire substrate with such materials, thereby increasing cost.

A further advantage of this invention is that the investment required to incorporate the apparatus into an existing line for manufacturing hygenic articles is small compared to the prior art. This is especially true if a pressure-sensitive melt adhesive is applied to the substrate, since its adhesive capacity is not time-dependent, and, therefore, the period between application of the adhesive to the substrate and then the absorbent particles to the adhesive may be timed according to the requirements of a particular manufacturing line. In addition, the apparatus of this invention is capable of operating at much higher speeds than prior art devices, which further reduces manufacturing costs.

DESCRIPTION OF THE DRAWINGS

The structure, operation and advantages of this invention will become further apparent upon consideration of the following description taken in conjunction with the accompanying drawings, wherein.

DETAILED DESCRIPTION OF THE INVENTION

Figure 1:
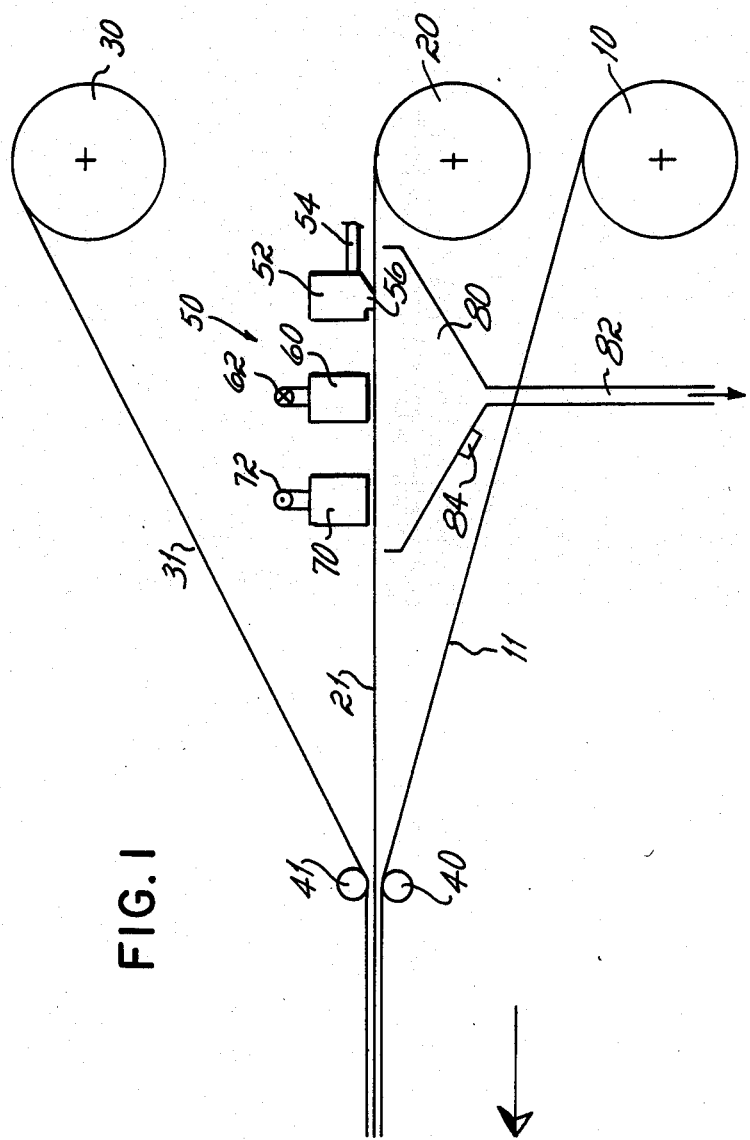
FIG. 1 is a schematic view of one embodiment of this invention for the production of three-layered tampons wherein absorbent particles are applied to a surface of one of the layers.

Referring now to the drawings, the apparatus of this invention is incorporated into a conventional device for the production of a hygenic article. The hygenic article manufacturing device is shown schematically in the figures and forms no part of this invention. As used herein, the term "hygenic articles" shall refer to diapers, sanitary napkins, tampons, incontinence pads, sickbed sheets and similar articles. Such articles generally include an inner layer formed of fleece or woven fabric which contacts the body, an outer, liquid-impermeable layer, and a core stratum therebetween for absorbing the eliminated body fluids. It should be understood, however, that the method and apparatus of this invention is equally applicable in the manufacture of muslin bandages, and other items which are non-hygenic such as filter inserts and the like.

Referring now to FIG. 1, the input area of a machine for the production of three-layer tampons is schematically illustrated. In this machine, three vertically spaced storage rollers 10, 20, 30 carry a laundry protector sheet 11, a core stratum 21 and a fleece cover layer 31, respectively. The layers 11, 21, 30 are drawn off of the storage rollers 10, 20, 30 in the direction of the arrow and meet at two pressure rollers 40, 41. Thereafter, the layers 11, 21, 31 are combined and cut at the appropriate length.

In one presently preferred embodiment of this invention, a device 50 is positioned above the moving core stratum 21 drawn from storage roller 20. The device 50 is approximately 50 centimeters in length and is readily mounted at the input area of a machine of the type shown in FIG. 1.

The device 50 includes at least one applicator head 52 for dispensing melt adhesive which is positioned above the core stratum 21. Adhesive is applied to the core stratum 21 through applicator head 52 by operation of an air jet 56 which is controlled by the control mechanism shown in FIG. 5 and discussed in more detail below. A measuring head 60 is disposed downstream from applicator head 52 in the direction of movement of core stratum 21, and is connected by a conduit 62 to an absorbent particle storage tank (not shown). Positioned directly above core stratum 21 downstream from measuring head 60 is suction head 70. The suction head 70 is connected by a suction pipe 72 to the suction side of a blower 74 (see FIG. 2). A container 80 is positioned beneath the core stratum 21 and device 50 and is connected through a conduit 82 to an absorbent particle storage tank. The container 80 is intended to collect oversprayed absorbent particles, as described below, for recirculation to the particle storage tank. A vibrator 84 is mounted on the base of the container 80 to induce movement of the absorbent particles from the container 80 into the conduit 82.

Figure 6:
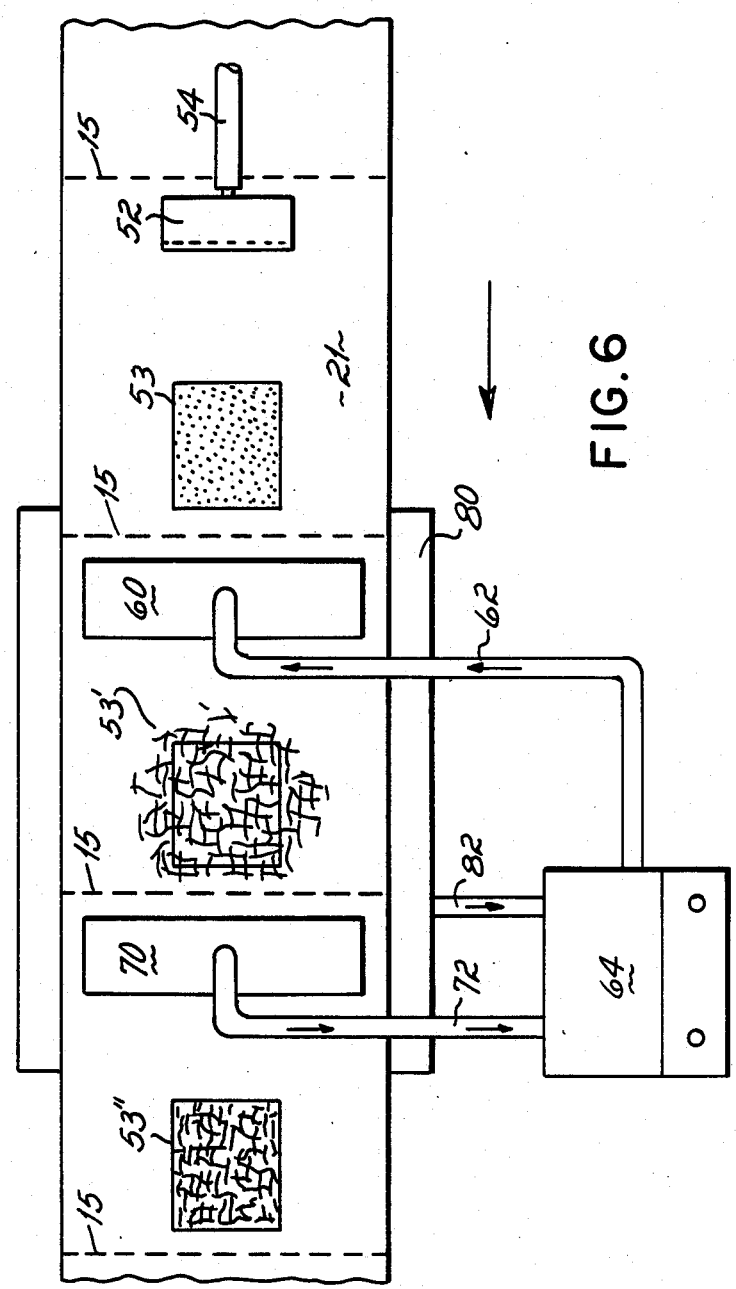
FIG. 6 is a schematic, plan view of the apparatus shown in FIG. 2.

Referring now to FIGS. 1 and 6, the operation of the device 50 according to this invention is as follows. The three layers 11, 21, 30 forming a hygenic article are drawn from their storage rollers 10, 20, 30 in the direction of the arrow in FIG. 1. The core stratum 21 passes beneath the device 50 and is combined with the other layers 11, 30 at the pressure rollers 40, 41. As described in more detail below, the control device of this invention transmits an impulse to the applicator head 52 to open air jet 56 and permit melt adhesive to flow from the applicator head 52 onto the facing surface of the core stratum 21. The air jet 56 is opened for a precise period of time, depending on the type of hygenic article to be manufactured, so that the melt adhesive applied to core stratum 21 forms a precisely defined area 53.

The core stratum 21 continues its movement to measuring head 60, which is also operated by the control device as described below. The operation of measuring head 60 is timed so that it releases absorbent material onto the area 53 of core stratum 21 which is coated with adhesive. Once the area 53 has passed the measuring head 60, release of the absorbent material is terminated until another area 53 arrives thereat. The duration of travel of area 53 between the applicator head 52 and measuring head 60 must be timed when using some types of melt adhesives so that the surface of the adhesive which coats area 53 is still viscous when it reaches the measuring head 60. A timing period of this type is not critical when using pressure-sensitive melt adhesive.

As shown in FIG. 6, the absorbent material released from measuring head 60 onto the core stratum 21 forms an area 53′ which moves toward the suction head 70. The area 53′ contains some absorbent material particles which have adhered to the adhesive covering area 53, and other absorbent material particles which lie on the core stratum 21 outside area 53. All of the excess particles of absorbent material which have not adhered to the adhesive covering area 53 are drawn off the core stratum 21 when it passes beneath suction head 70. The excess absorbent material passes through suction line 72 to a suction and pump feeding device 64, which is also connected to conduit 82 formed at the base of container 80 (see FIG. 2). A sharply defined area 53″ on core stratum 21 is thus formed after it passes beneath suction head 70 which carries a predetermined quantity of finely distributed absorbent material. The core stratum 21 then continues its movement beyond suction head 70 for combination with the layers 11, 31 at the pressure rollers 40, 41.

Figure 2:
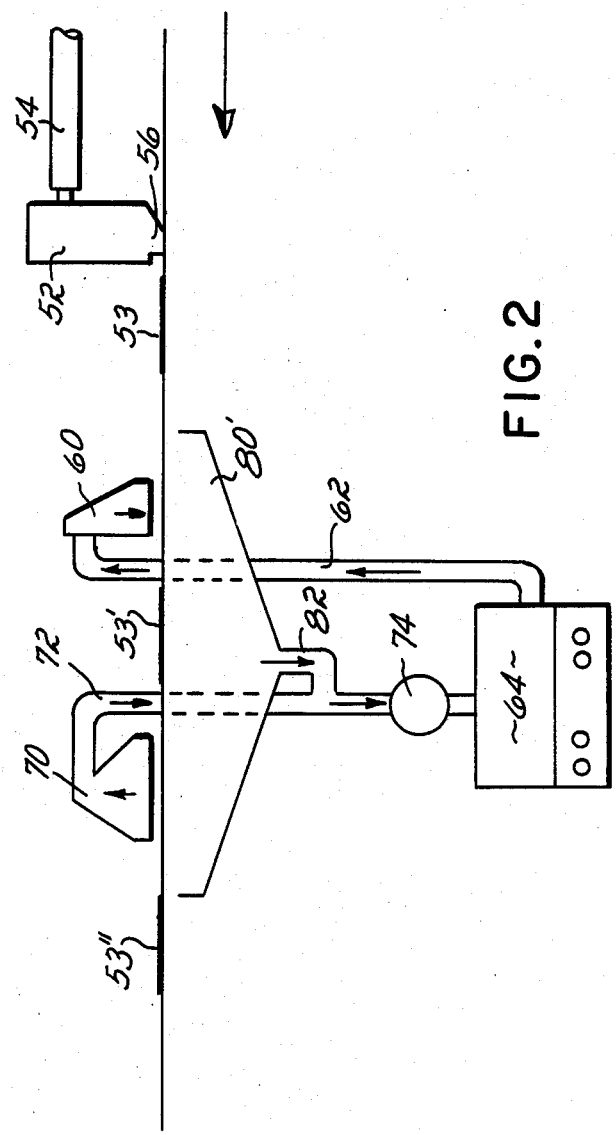
FIG. 2 is a schematic view of an alternative embodiment of the system shown in FIG. 1.
Figure 3:
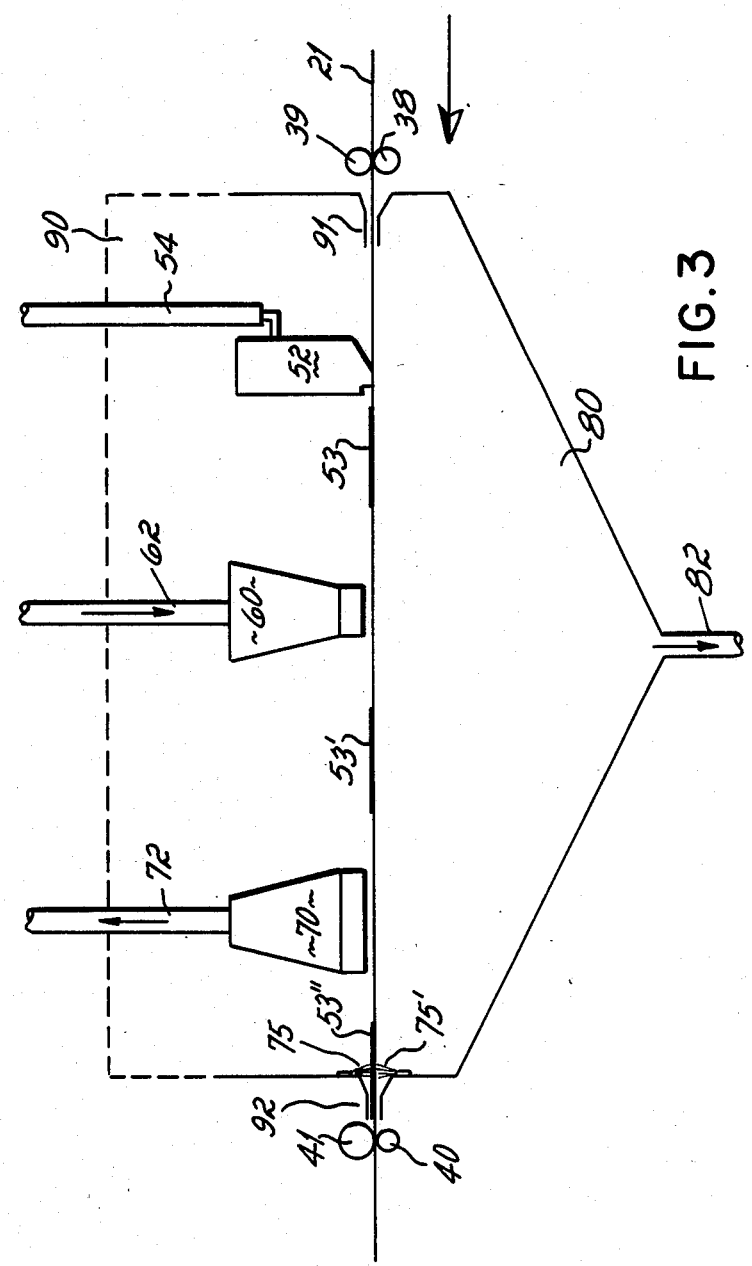
FIG. 3 is a schematic view of another alternative embodiment of this invention.

Alternative embodiments of the device according to this invention shown in FIGS. 1 and 6, are illustrated in FIGS. 2 and 3. Considering FIG. 2, a container 80' is disposed beneath the measuring head 60 and suction head 70, but not beneath the applicator head 52. In addition, the embodiment of FIG. 2 incorporates a blower 74, operable independently of feed device 64, which is connected both to the conduit 82 of container 80' and the suction line 72 of suction head 70. All other aspects of this embodiment are essentially identical to the embodiment of FIGS. 1 and 6.

The embodiment shown in FIG. 3 is similar to FIG. 1 except for the addition of a cover 90 mounted above the core stratum 21 and heads 52, 60, 70. The height of cover 90 is determined by the size of heads 52, 60, 70. The cover 90 and container 80 together form a housing which is arranged between the pressure rollers 40, 41 and a pair of pressure rollers 38, 39 positioned upstream along core stratum 21 relative to the applicator head 52. The core stratum 21 is received within the housing of this embodiment through an intake slot 91 and exits from the housing through an outlet slot 92. The applicator head 52, measuring head 60 and suction head 70 operate in the same manner in this embodiment as described above in the embodiment of FIGS. 1 and 6. In addition to suction head 70, the embodiment of device 50 shown in FIG. 3 incorporates a pair of brushes 75, 75' which are disposed downstream from suction head 70 on opposite sides of core stratum 21 within the housing. The brushes 75, 75' contact the core stratum 21 and sweep any excess absorbent particles, which were not drawn off by the suction head 70, directly into the container 80.

Each of the embodiments shown in FIGS. 1, 2 and 3 provide no support such as a conveyor belt or table for the core stratum 21 as it moves beneath applicator head 52. This facilitates the application of a uniform film of adhesive to the core stratum 21.

Figure 5:
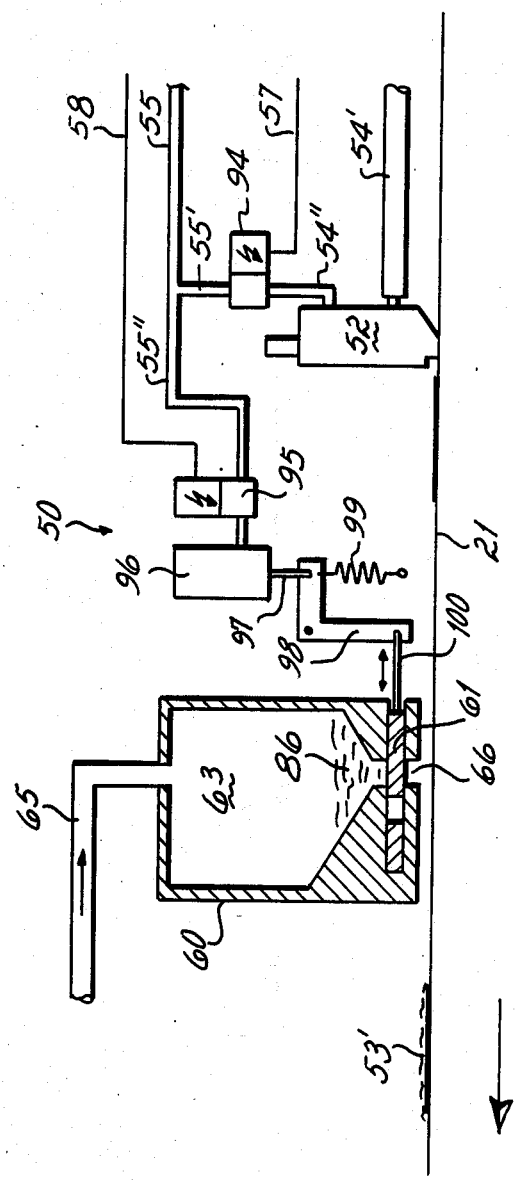
FIG. 5 is a schematic view of a control device according to this invention.

Referring now to FIG. 5, a presently preferred embodiment of a control device is illustrated for controlling the applicator head 52 and measuring head 60 in the embodiments of device 50 shown in FIGS. 1-3 and 6.

Considering first the operation of applicator head 52, reference is made to the righthand portion of FIG. 5. Fluid melt adhesive is supplied to applicator head 52 by a melt adhesive line 54' which is connected to an adhesive storage tank (not shown). The fluid adhesive supplied by line 54' is dispensed from applicator head 52 by operation of a solenoid valve 94. The solenoid valve 94 is connected through a branch line 55' to a pressure line 55 maintained under continuous pressure. A line 54" connects the solenoid valve 94 with the applicator head 52. In response to a signal provided through line 57, the solenoid valve 94 is opened to permit line pressure from line 55 to pass through the solenoid 94 into line 54" and then to applicator head 52. The applicator head 52 is of conventional construction, and includes a pressure medium valve (not shown) which is actuated by the line pressure transmitted through line 54" and is operable to open air jet 56 of the release of adhesive from applicator 52. The signal supplied by line 57 which activates solenoid 94 is timed so that adhesive is applied through applicator head 52 over a precisely defined area 53 of core stratum 21. At the predetermined end of area 53, the solenoid valve 94 is closed to stop the adhesive flow through applicator head 52.

Referring now to the lefthand portion of FIG. 5, the operation of measuring head 60 is illustrated. A branch line 55" from pressure line 55 connects to a second solenoid 95 whose operation is controlled by a signal supplied through line 58. Second solenoid valve 95 is connected to a control cylinder 96 having a piston rod 97 operatively connected to one arm of an angle lever 98. The other arm of angle lever 98 is connected through rod 100 to a slide 61. The slide 61 is disposed across an outlet slot 66 formed at the base of a storage room 63 in measuring head 60 which contains a pool of absorbent particles 86. The slide 61 is movable between an idle position wherein the outlet slot 66 is closed, and an open position wherein absorbent particles 86 are released from measuring head 60 through outlet slot 66.

Once the leading edge of area 53 reaches the measuring head 60, a signal supplied by control line 58 opens solenoid valve 95 so that line pressure from line 55 and branch line 55" flows into the cylinder 96. When the cylinder 96 is pressurized, its piston rod 97 moves upwardly causing the arm 98 to pivot and move slide 61 to an open position in which absorbent particles are permitted to emerge through slot 66. The signal supplied through control line 58 is terminated to close solenoid valve 95 when the entire area 53 has passed the slot 66 and is covered with absorbent particles 86. A spring 99 attached to the angle lever 98 is then operable to return the angle lever 98 to an upright position, shown in FIG. 5, wherein the slide 61 closes slot 66. Area 53', which is the area 53 covered with absorbent particles 86, continues to the suction head 70 as shown in FIGS. 1-3. The suction head 70 need not be actuated by a special control device since it generally operates continuously.

Figure 7:
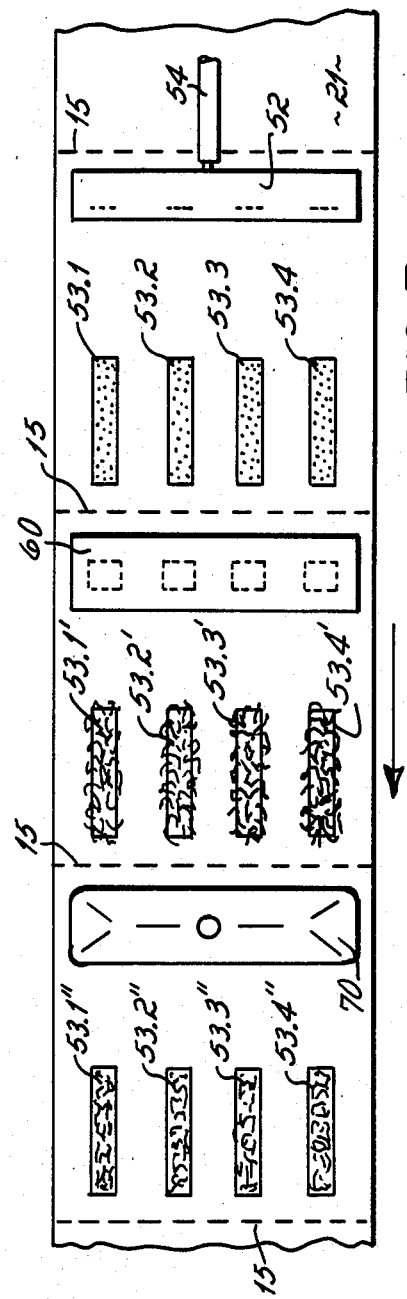
FIGS. 7 and 8 are schematic plan views of a layer of a hygenic article having different areas coated with melt adhesive.
Figure 8:
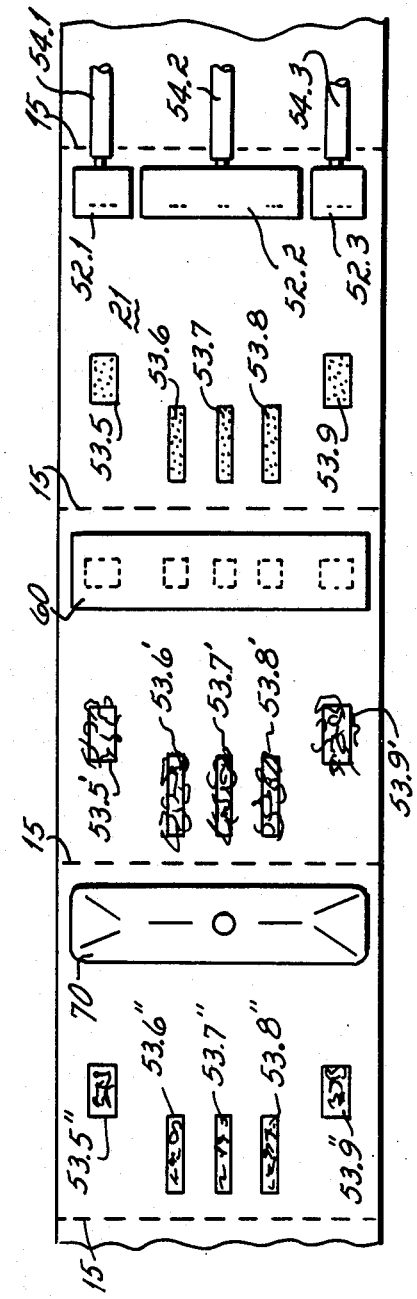

Referring now to FIGS. 7 and 8, the device 50 of this invention may be modified and controlled with a control device of the general type shown in FIG. 5, to produce staggered areas 53.1 to 53.4 and 53.5 to 53.9, respectively, for coating with absorbent particles.

In FIG. 7, four adhesive areas 53.1 to 53.4 of equal size are spaced across the width of core stratum 21. In contrast, the areas 53.5 to 53.9 of FIG. 8 are offset from one another and areas 53.5 and 53.9 differ in size from areas 53.6 to 53.8. The construction of applicator head 52 to produce such adhesive areas 53.1 to 53.4, and applicator heads 52.1 to 52.3 to produce adhesive areas 53.5 to 53.9, are known and are not discussed herein since they do not form a part of this invention.

The width of adhesive areas 53.1 to 53.9 are determined by the width of the air jets 56 within applicator heads 52 and 52.1 to 52.3, and their length is set by the control device taking into account the rate of feed of the core stratum 21. For example, in FIG. 8, three applicator heads 52.1 to 52.3 are illustrated which are each controlled by the control device to produce the adhesive areas 53.5 to 53.9. Each of the applicator heads 52.1, 52.2, 52.3 are supplied melt adhesive through separate feed lines 54.1, 54.2 and 54.3, respectively. A single feed line 54 supplies melt adhesive to applicator head 52 of FIG. 7.

Both of the measuring heads 60 in FIGS. 7 and 8 include spaced outlets for the release of absorbent material onto the core stratum 21. Alternatively, measuring heads 60 may be formed with a single outlet for release of the absorbent material over substantially the entire width of core stratum 21 to form areas 53.1' to 53.9'. Suction heads 70 of FIGS. 7 and 8 are continuously operated to draw excess absorbent material from the adhesive areas 53.1' to 53.9' to form the finished areas 53.1" to 53.9" downstream from the suction head 70. The dotted lines 15 shown in FIGS. 7 and 8 represent areas where the core stratum 21 may be cut to form individual articles.

Figure 4:
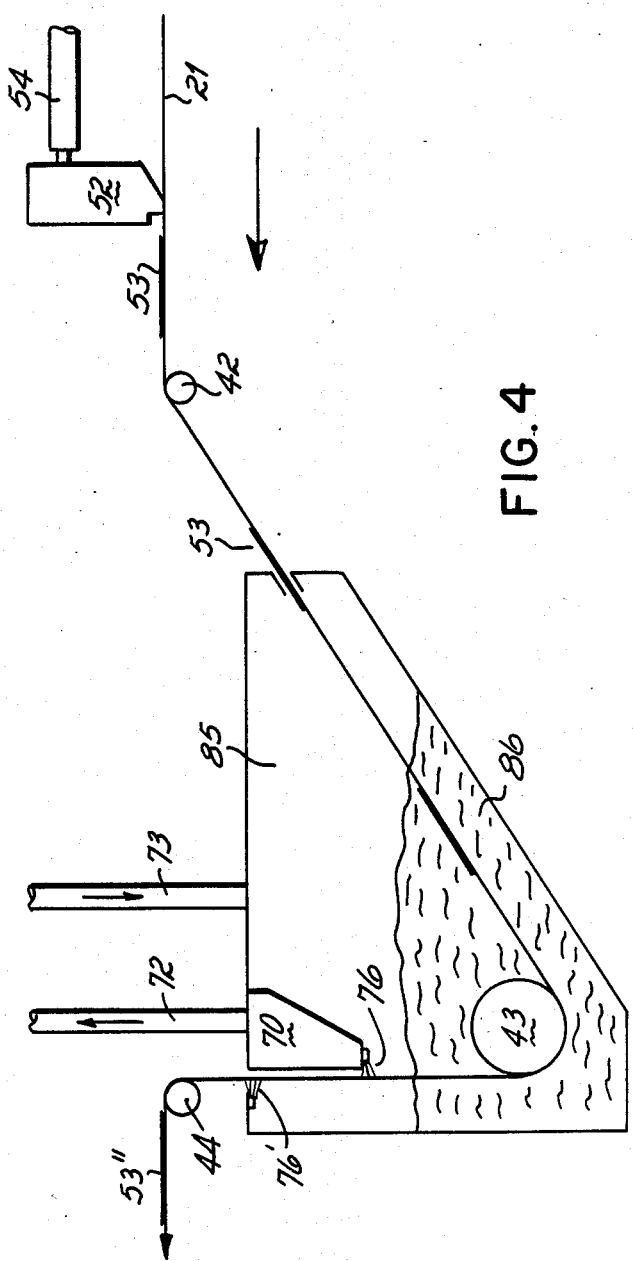
FIG. 4 is a still further alternative embodiment of this invention in which the substrate is immersed within a pool of absorbent material.

Referring now to FIG. 4, an alternative embodiment of the device according to this invention is illustrated. In this embodiment, the measuring head 60 is eliminated and replaced with a container 85 filled with a pool of absorbent particles 86.

An applicator head 52 of the type described above is operable to apply a thin film of melt adhesive to the core stratum 21 forming areas 53 coated with adhesive. After passing the applicator head 52, the core stratum 21 moves over a guide roller 42 and then downwardly through an inlet formed in the container 85. The core stratum 21 then moves beneath another guide roller 43, which is immersed in the absorbent particles 86 within container 85, and turns vertically upwardly through an outlet formed at the top of container 85. The core stratum moves over a roller 44 which is spaced above roller 43 and disposed outside of container 85, and then continues on for further processing in a machine for forming hygenic articles. The core stratum 21 is therefore completely immersed in the pool of absorbent particles 86 within container 85 so that at least a portion of the particles adhere to the areas 53 covered with adhesive.

The container 85 is preferably filled with absorbent particles 86 to a predetermined height, and a pair of brushes 76, 76', and a suction head 70, are disposed in the space between the top of container 85 and the top surface of the absorbent particles 86. Since both surfaces of the core stratum 21 are exposed to the absorbent particles, both surfaces of the core stratum 21 must be thoroughly cleaned after it emerges from the pool of absorbent particles 86. The brushes 76, 76' are disposed on opposite sides of the core stratum 21 and contact both of its surfaces to sweep off excess absorbent particles 86 which have not adhered to the adhesive areas 53 and which have been deposited on the opposite surface of core stratum 21. Since the brushes 76, 76' are disposed within the container 85, the excess absorbent particles 86 fall directly back into the pool of absorbent particles 86. In addition, any excess particles not removed by the brushes 76, 76' are drawn off of the core stratum 21 by the suction head 70 and then flow to a blower (not shown) whose feed line 73 returns to conveyor 85. The feed line 73 also serves to deliver fresh absorbent material into container 85 at appropriate intervals.

Although the operation of the device 50 described above was discussed in connection with applying absorbent material to the core stratum 21, it should be understood that other layers of the hygenic articles could be similarly treated. In addition, the number and orientation of the applicator and/or measuring heads can be adjusted to produce articles such as bandages and the like. The removal of excess absorbent particles from the stratum may also be achieved other than by suction or brushes, e.g., through a shaking motion imparted to the stratum by appropriate means.

While I have disclosed specific embodiments of my invention, persons skilled in the art to which this invention pertains will readily appreciate changes and modifications which may be made to the invention. Therefore, I do not intend to be limited except by the following appended claims.

What is claimed is:

1. Apparatus for applying and securing absorbent material particles to at least one of the front and back surfaces of a substrate which forms one or more layers of an hygenic article, comprising:
    adhesive applicator means for applying a uniform, melt adhesive film to selected areas of the substrate in a predetermined pattern;
    a container having top, bottom and side sections forming an enclosed interior partially filled with a pool of absorbent material particles said container being formed with a substrate inlet and a substrate outlet;
    means for moving the substrate from said adhesive applicator means into said substrate inlet and out said substrate outlet of said container, the front and back surfaces of the substrate being completely immersed in the pool of absorbent material particles in the course of passage through said container such that the absorbent material particles adhere to said selected areas of the substrate covered with adhesive; and
    means mounted in said enclosed interior of said container for contacting the substrate and removing excess absorbent material particles from the substrate not adhered to said selected areas covered with adhesive, said excess absorbent material removed from the substrate falling back into the pool of absorbent material particles.

2. The apparatus of claim 1 in which said means contacting the substrate for removing excess absorbent material particles includes brush means for sweeping excess absorbent material particles therefrom.

3. The apparatus of claim 1 further comprising suction means for removing absorbant material particles not adhered to said selected areas of the substrate covered with adhesive, said suction means being disposed within said container and communicating with an absorbent material return line operable to return absorbent material particles removed by said suction means back into said container.

4. A method of applying and securing absorbent material to at least one of the front and back surfaces of a moving substrate which forms one or more layers of an hygenic article, comprising:
    applying a thin layer of adhesive onto selected areas of the substrate in a predetermined pattern;
    guiding the substrate carrying the adhesive through an inlet passage into the substantially closed interior of a container partially filled with a pool of abosrbent material particles;
    immersing both the front and back surfaces of the substrate carrying the adhesive within the pool of absorbent material particles in said container so that absorbent material particles adhere to said selected areas of the substrate coated with adhesive;
    contacting the substrate with means mounted in said interior of said container for removing absorbent material particles from the substrate not adhered to said spaced areas covered with adhesive before the substrate leaves the container; and
    collecting in said container the absorbent material particles removed from the substrate.

5. The method of claim 4 wherein said step of removing absorbent material particles not adhered to the substrate is accomplished at least in part by applying a suction to the substrate before the substrate exits said container.

* * * * *